United States Patent [19]

Kitajima

[11] Patent Number: 5,336,599
[45] Date of Patent: Aug. 9, 1994

[54] METHOD OF MEASURING ANALYTE USING DRY ANALYTICAL ELEMENT

[75] Inventor: Masao Kitajima, Saitama, Japan
[73] Assignee: Fuji Photo Film Co., Ltd., Kanagawa, Japan
[21] Appl. No.: 167,629
[22] Filed: Dec. 15, 1993

Related U.S. Application Data

[63] Continuation of Ser. No. 916,944, Jul. 20, 1992, abandoned.

[30] Foreign Application Priority Data

Jul. 19, 1991 [JP] Japan .................... 3-203738

[51] Int. Cl.$^5$ .................. C12Q 1/48; G01N 31/22; G01N 21/77
[52] U.S. Cl. ........................ 435/15; 422/58; 435/4; 435/16; 436/63; 436/164; 436/165; 436/170
[58] Field of Search ............... 422/55, 56, 58; 435/4, 435/7.4, 15, 16; 436/63, 66, 71, 170, 164, 165

[56] References Cited

U.S. PATENT DOCUMENTS

| | | | |
|---|---|---|---|
| 3,992,158 | 11/1976 | Przybylowicz et al. | 422/56 |
| 4,066,403 | 1/1978 | Bruschi | 436/170 X |
| 4,258,001 | 3/1981 | Pierce et al. | 422/56 |
| 4,292,272 | 9/1981 | Kitajima et al. | 422/56 X |
| 4,521,520 | 1/1985 | Jacke | 436/66 |
| 4,540,670 | 9/1985 | Arai et al. | 436/170 |
| 4,548,906 | 10/1985 | Sekikawa et al. | 436/170 X |
| 4,559,949 | 12/1985 | Levine | 436/66 X |
| 4,578,358 | 3/1986 | Oksman et al. | 436/66 |
| 4,578,359 | 3/1986 | Oksman et al. | 436/66 |
| 4,719,181 | 1/1988 | Schobel et al. | 436/66 |
| 4,786,595 | 11/1988 | Arai et al. | 436/170 X |
| 4,806,311 | 2/1989 | Greenquist | 422/56 |
| 4,870,005 | 9/1989 | Akiyoshi et al. | 436/170 X |
| 4,871,679 | 12/1989 | Tanaka et al. | 436/79 |
| 4,889,797 | 12/1989 | Amono et al. | 435/4 |
| 4,902,477 | 2/1990 | Katsuyama et al. | 436/170 X |
| 4,919,890 | 4/1990 | Arai et al. | 436/170 X |
| 4,939,085 | 7/1990 | Arai | 436/170 X |
| 4,975,366 | 12/1990 | Sudo et al. | 436/170 X |
| 4,990,457 | 2/1991 | Tanaka et al. | 436/170 |
| 5,008,078 | 4/1991 | Yaginuma et al. | 436/170 X |
| 5,013,527 | 5/1991 | Arai et al. | 436/71 X |
| 5,019,347 | 5/1991 | Hiratsuka et al. | 436/170 X |
| 5,023,052 | 6/1991 | Nagamoto et al. | 436/170 X |
| 5,059,349 | 10/1991 | Phillips et al. | 436/36 X |
| 5,118,472 | 6/1992 | Tanaka et al. | 436/170 X |
| 5,122,451 | 12/1992 | Tanaka et al. | 422/58 X |
| 5,219,762 | 6/1993 | Katamine et al. | 422/58 X |

*Primary Examiner*—Jill A. Johnston
*Assistant Examiner*—Milton I. Cano
*Attorney, Agent, or Firm*—McAulay Fisher Nissen Goldberg & Kiel

[57] ABSTRACT

A method for measuring an analyte using a dry analytical element composed of at least a hydrophilic polymer layer and a spreading layer laminated onto a water-impermeable support and to which a liquid sample of the analyte has been supplied, by supplying a measuring reagent solution to the analytical element. The measurement of the analytical element is carried out by optical means.

13 Claims, 6 Drawing Sheets

FIG. 1

← Spreading Layer
← Hydrophilic Polymer Layer
← Water-Impermeable Support

FIG. 2

← Spreading Layer
← Reflecting Layer
← Hydrophilic Polymer Layer
← Water-Impermeable Support

FIG. 3

← Spreading Layer
← Barrier Layer
← Hydrophilic Polymer Layer
← Water-Impermeable Support

FIG. 4

← Spreading Layer
← Barrier Layer
← Hydrophilic Polymer Layer
← Mordant Layer
← Water-Impermeable Support

METHOD OF MEASURING ANALYTE USING DRY ANALYTICAL ELEMENT

This is a continuation of application Ser. No. 07/916,944, filed Jul. 20, 1992 now abandoned.

BACKGROUND OF THE INVENTION

This invention relates to a method of measuring an analyte in a liquid sample using a dry analytical element which does not contain reagents capable of reacting directly with the analyte to produce a measurable change.

It has been conducted from a long ago to diagnose human diseases by analyzing blood, urine or the like.

As a method therefor, there is the wet analysis using a solution reagent. This method has a long history, and various detecting reagents have been developed for many items. Various analyzers have also been developed which are compact apparatuses to big scale apparatuses. Samples used for the wet analysis are plasma, serum, urine and the like, but whole blood samples are in general not used as it is.

In the wet analysis, reagents can be divided into several groups by considering their stability during stock, and dissolved and mixed at the time of use. It is also possible to divide the addition of respective reagents into several steps.

Moreover, since it is possible to prepare a suitable amount of each reagent by dissolving according to the number of samples to be measured, the measuring cost per one sample is reduced. It is troublesome to automate the measurement by combining the treatment of many solutions. However, there is a history to develop clinical analytical apparatuses, and various automatic apparatuses having a good efficiency have already been developed and put to practical use in every field requiring big, middle, small treating capacity according to great social requirement.

Disadvantages of the wet analysis are in the preparation and supply of samples. Since this method is composed on the premise of the measurement of transmitted light through a transparent solution, whole blood samples cannot be used as the samples to be measured without pretreatment. That is, after drawing whole blood samples, they are centrifuged, and the plasma or serum which is the supernatant is put into a sample cup, or the centrifuge tube as it is set in a measuring apparatus instead of the sample cup. In addition to the complexity in the above operations, there is a further problem that it is necessary to keep a great amount of whole blood samples for separating a sufficient amount of plasma or serum without contamination of red blood cells.

In order to obtain 200 $\mu l$ of a plasma sample by centrifuging, usually, 1.5 to 2 ml of whole blood is necessary. Even though centrifuging and aftertreatment are conducted carefully, a minimum amount of whole blood is estimated to be about 500 $\mu l$.

On the other hand, a necessary amount of a sample is about 10 $\mu l$ per one analytical item for the measurement, and accordingly, it is only 100 $\mu l$ for 10 items and 200 $\mu l$ for 20 items. Nevertheless, 2 to 20 ml of blood is actually drawn in hospitals or the like, that is, 50 to 100 times as much as the necessary plasma amount is drawn. Every person, even a healthy person, suffers with pain mentally and physically by inserting the needle of a syringe into blood tube and drawing blood. Particularly, persons having thin tubes constitutionally and sicky persons suffer with pain accompanied with drawing beyond imagination, and patients who are repeatedly drawn greatly desire to reduce the amount of blood drawn minumum.

Insidentally, in the blood drawing room of hospitals, medical practitioners and clinics, whole blood samples drawn and put into a tube or a vacuum syringe are transported as it is or in cooled conditions to a central assay room or an assay center. That is, each blood is centrifuged after transportation, and separated into solid components such as red blood cells and plasma or serum which is used as the analytical sample. During the transportation, there is a possibility that biochemical reactions affecting the analysis proceed by the coexistance of red blood cells, but countermeasures are taken only against the variation factors which are known to affect analytical results remarkably great, such as inhibition to glycolysis and anticoagulation.

By taking the above matters into consideration, it is preferred that centrifuging is conducted immediately after blood drawing, but this is usually not done. Because, analytical methods using blood serum as the sample have been established historically, and it is necessary for the separation of serum to complete coagulation by leaving at least for 30 minutes to 1 hour. Moreover, when blood is centrifuged after adding an anticoagulant, according to samples, fibrins occasionally deposit between the centrifugation and the measurement by an analyzer. The above matters are liable to induce troubles in the transferring system, such as piperting syringe or tubes in the analyzer.

Accordingly, it is desirable to obtain serum samples by centrifuging within about 1 hour after drawing blood. However, although it is possible in the assay in hospitals, in the case of assay centers requiring a time for the transportation of samples, the time when centrifuging is conducted quite varies, and the centrifuging is often conducted after one day or more.

As an analytical method which has conquered the disadvantages accompanied with the preparation and supply of samples, many dry analytical elements (also called analytical film, multilayer test strip, or the like) have been developed wherein all reagents necessary for qualitative or quantitative analysis are incorporated into a test paper or an analytical element such as multilayer anlaytical film, and are sold.

The dry analytical elements have the following characteristics.

1) All reagents necessary for analysis are incorporated into an analytical element.

2) Reactions necessary for analysis occur merely by spotting a sample (usually, plasma, serum or urine, as to partial items, whole blood).

The dry analytical elements are roughly divided into 3 groups according to their utilization field.

Group 1: The object is in screening by practitioners and at homes, and the results can be judged qualitatively (+/−) or semiquantitatively (about 5 degrees) by visual inspection.

Group 2: Measuring place can be relatively freely selected by combining an analyzer characterized by compact size and simple operation. Used in emergency assay rooms, childhood wards, practitioners, small scale hospitals, etc.

Group 3: Used for measuring routine assays in hospitals or assay centers using a fully automatic analyzer.

The construction and content of the anlaytical elements are different according to the above classification.

Representative analytical elements belonging to Group 1 are urine test paper and blood sugar test paper. Analytical operations of these papers are simple, and analyzer is not necessary. However, the results are rough (such as normal or abnornal), and it is premised that, in the necessary case, sample is measured again by another analytical means capable of obtaining a quantitative result.

In the analytical elements according to this method, operations by a specialist, such as clinical assay engineer, medical doctor and nurse, are not premised, and commonly, it is composed so that urine or whole blood can be used as a sample without any pretreatment.

The object of the analytical elements belonging to Group 2 is in quantitative analysis, and quantitative measurement by an apparatus is premised. Operation is relatively simple, although it is not simpler than Group 1, a specialyst such as a clinical assay engineer is not premised. As to samples, analytical elements to which anyone of whole blood, plasma, serum or urine is applicable have gradually been developed, but analytical items measurable by whole blood are still 10 and several items which are relatively restricted.

The samples applicable to fully automatic analyzers in Group 3 are, in general, limited to plasma, serum and urine, and whole blood cannot be used as the sample. However, measurable items have gradually been increased, and analytical elements have already been developed for measuring at least 40 items.

However, in the dry analytical elements, all reagents necessary for reactions must be incorporated into the analytical element. Nevertheless, the characteristic of the reagents are different respectively according to analytical items, and as a result, there is a great problem that much labor, time and equipment cost are consumed by developing recipe and optimiizing manuacturing conditions.

Besides, since all reagents are contained, it is necessary to keep sufficiently dry conditions for the stock of the analytical elements for a long period. For that purpose, usually, each analytical element is packed by a moistureproof package, and if necessary, a drying agent is put in the package.

Even when the dry package and cooling preservation are employed, shelf life is only 1 to 2 years which elevates the price of the dry analytical elements.

SUMMARY OF THE INVENTION

An object of the invention is to provide a method of measuring an analyte capable of providing an accurate result by a simple operation using a dry analytical element which can be prepared in a simple process, which can be preserved for a long period, and which can use a very small amount of a body fluid, such as whole blood, plasma, serum or urine, as the sample.

Another object of the invention is to provide a method of preserving and transporting an analytical element, to which a body fluid such as blood, a biological sample or an aqueous solution sample is supplied, with keeping a sufficient analytical accuracy.

Another object of the invention is to provide a method capable of measuring an analytical element supplied with a sample and then preserved, even in the case that a rate assay is necessary, such as enzyme reaction.

The present invention provides methods of measuring an analyte using a dry analytical element which have achieved the above objects, which comprises, a process of supplying a measuring reagents solution to the analytical element comprising at least a hydrophilic polymer layer and a spreading layer laminated onto a water-impermeable support and not containing the measuring reagents to which a liquid sample has been supplied and thereby reaction occuring, and a process of measuring the analytical element wherein the reaction occurred by an optical means.

DETAILED DESCRIPTION OF THE INVENTION

The spreading layer has a function to spread components contained in an aqueous liquid sample in plane without uneven distribution and to supply them to the hydrophilic polymer layer at a constant rate per an unit area, and may be composed of every nonfibrous or fibrous porous material known for the spreading layer of conventional dry analytical elements. Examples of the spreading layer includes nonporous isotropic microporous medium layers represented by membrane filter (blushed polymer) disclosed in U.S. Pat. No. 3,992,158, nonfibrous porous layers represented by continuous space-containing three dimensional lattice grain structure layer where polymer particulates are joined at spots by a water-nonswelling adhesive disclosed in U.S. Pat. No. 4,258,001, porous layers composed of woven fabric disclosed in U.S. Pat. No. 4,292,272, GB 2,087,074A, etc., porous layers composed of knitted fabric disclosed in EP 0,162,302A and the like.

The spreading layer may be composed of two or more microporous layers as disclsed in EP 0,166,365A, EP 0,226,465A, etc. As to the multilayer analytical element wherein two or more porous layers are superposed, it is necessary to have the construction that all layers are integrally laminated at the time of sample spotting, but it is not necessary to be integrated in the subsequent processes. Optionally, the analytical element can be used in the state that the first porous layer is separated from the second porous layer.

The spreading layer may contain a nonionic, anionic, cationic or ampholytic surfactant in order to accelerate spreading of a sample. Besides, it may contain a spreading controller, such as hydrophilic polymer for the purpose of controlling spreading. Furthermore, it may contain all or a part of various reagents for accelerating the object detecting reaction or reducing or inhibiting interfering reactions.

A suitable thickness of the spreading layer is 20 to 200 $\mu$m, preferably 50 to 170 $\mu$m, more preferably 80 to 150 $\mu$m.

The hydrophilic polymer layer may be composed of various known polymers which are water-soluble, swellable and hydrophilic and are used for conventional dry analytical elements. The hydrophilic polymer is generally a natural or synthetic hydrophilic polymer having a swelling ratio in the range of about 1.5 to about 20 times preferably from about 2.5 to about 15 times at water absorption at 30° C. Examples of the hydrophilic polymer are gelatines, such as acid-treated gelatin and deionized gelatin, gelatin derivatives, such as phthalated gelatin and hydroxyacrylate-graft gelatin, agarose, pullulan, pullulan derivatives, polyacrylamide, polyvinyl alcohol and polyvinylpyrrolidone. Instead of the hydrophilic polymer layer, paper or porous polymer membrane having hydrophilic surface can be used.

A suitable thickness of the hydrophilic polymer layer is about 1 to 100 $\mu$m, preferably about 3 to 50 $\mu$m, more preferably about 5 to 30 $\mu$m. It is preferred that the hydrophilic layer is substantially transparent. The hydrophtlic polymer layer may contain all or a part of various reagents for accelerating the object detecting reaction or reducing or inhibiting interfering reactions.

The water-impermeable support may be a known water-impermeable support used in conventional dry analytical elements, and includes a transparent film made of polyethylene terephthalate, polycarbonate of bisphenol A, polystyrene, cellulose ester, such as, cellulose diacetate, cellulose triacetate or cellulose acetate propionate, or the like. The thickness of the support is usually in the range of about 50 $\mu$m to about 1 mm, preferably from about 80 $\mu$m to about 300 $\mu$m. The support is usually light-transmissive, but in the case of measuring from the spreading layer side, it may be colored or may be opaque. The support may be provided with an undercoating layer on its surface in order to strengthen the adhesion of the hydrophilic polymer layer.

In the method of the invention, the analyte to be measured is not limited, and any analyte usually measured in clinical assay field of which the analytical method has already established can be measured, such as enzymes, lipids, inorganic ions, metabolites, proteins, various components derived from living body, such as globulins, antigens and antibodies, medicines, hormones and tumor markers.

The dry analytical element used in the invention may have various constructions described below according to the analytical item or the sample to be measured. Some fundamental layer constructions are shown in FIGS. 1–4.

1. Analytical element having a layer construction of water-impermeable suport/hydrophilic polymer layer/spreading layer:

This analytical element is effective for the analysis of Ca, GOT (glutamic-oxaloacetic transaminase), GPT (glutamic-pyruvic transaminase), $\gamma$-GTP ($\gamma$-glutamyl transpeptidase), glucose, LDH (lactate dehydrogenase), CPK (creatine phosphokinase), TP (total protein), Alb (albumin), Tcho (total cholesterol), UA (uric acid), neutral fats, etc.

2. Analytical element having a layer construction of water-impermeable support/hydrophilic polymer layer/spreading layer and containing chromogen in hydrophilic polymer layer and/or spreading layer:

The chromogen applicable to the invention includes 4-aminoantipyrines (synonym: 4-aminophenazone, i.e. 1-phenyl-2,3-dimethyl-4-amino-3-pyrazoline-5-one) disclosed in Ann, Clin. Biochem., 6, 24–27 (1969), and 4-aminoantipyrine analogs, such as tri-substituted-4-amino-3-pyrazoline-5-one such as 1-(2,4,6-trichlorophenyl)-2,3-dimethyl-4-amino-3-pyrazoline-5-one and 1-(3,5-dichloropheynyl)-2,3-dimethyl-4-amino-3-pyrazoline-5-one disclosed in EP 0,103,901A, and 1-phenyl-2,3-dimethyl-4-dimethylamino-3-pyrazoline-5-one disclosed in U.S. Pat. No. 3,886,045. Preferred compounds are 4-aminoantipyrine, 1-(2,4,6-trichlorophenyl)-2,3-dimethyl-4-amino-3-pyrazoline-5-one, 1-(3,5-dichlorophenyl)-2,3-dimethyl-4-amino-3-pyrazoline-5-one, and the like.

3. Analytical element having a layer construction of water-impermeable support/hydrophilic polymer layer/spreading layer and containing chromogen and other reagents (excluding the measuring reagent described later) in hydrophilic polymer layer and/or spreading layer:

Examples of the other reagents are POP (peroxidase), NAD (nicotinamide adenine dinucleotide), NADP (nicotinamide adenine dinucleotide phosphate), DIP (diaphorase), etc.

In the above constructions of 2 and 3, the chromogen and the other reagents can be supplied after a liquid sample is supplied and then stabilized. This is preferable, because most of the chromogens are water-insoluble and therefore it is necessary to add separately. Better reproducibility can be obtained by preparing the analytical element wherein the chromogert and the other reagents are previously incorporated into the prescribed layer.

4. Analytical element containing mordant:

In the case that the coloring reagent forms an ionic dye, a mordant layer may be provided between the water-impermeable support and the reagent layer. The efficiency of optical detection can be improved by transferring the dye produced in proportion to the quantity of analyte in a sample to the mordant layer and trapping it there.

For example, in the case of forming a cationic dye by coloring reagents, a hydrophilic polymer layer containing a polymer having an anionic atom or atomic group bound to the polymer chain can be used as the mordant layer. In the case of forming an artionic dye by coloring reagents, a hydrophilic polymer layer containing a polymer having a cationic atom or atomic group bound to the polymer chain can be used.

The mordant polymers are described in detail in Japanese Patent KOKOKU No. 2-30466, U.S. Pat. Pat. Nos. 4,042,335, 4,166,093, 4,144,306, etc.

For example, anionic mordant polymers are alkali hydrolyzate of methyl vinyl ether-maleic anhydride copolymer, alkali metal salt or alkaline earth metal salt of polystyrene-p-sulfonic acid, alkali metal salt or alkaline earth metal salt of a copolymer of styrene-p-sulfonic acid and hydrophilic vinyl monomer, and the like disclosed at columns 13–14 of Japanese Patent KOKOKU No. 2-30466. The Japanese patent further discloses layers capable of incorporating the above polymers at columns 15–16.

5. Analytical element having a layer construction of the above 1–4 provided with light-shielding layer between hydrophilic polymer layer and spreading layer:

Whole blood samples can be used as it is. The light-shielding layer is a water-permeable layer where particulates having light-shielding ability or light-shielding ability and light-reflecting ability are dispersed in and supported by small amount of a hydrophilic polymer binder having film-forming ability. The light-shielding layer shields the color of an aqueous liquid sample, particularly red color of hemoglobin contained in a whole blood sample, when the detectable change (color change, coloring, etc.) is measured by reflection photomerry from the light-transmissive support side, and also functions as a light-reflecting layer or a background layer.

Particulates having light-shielding ability and light-reflecting ability include titanium dioxide particulates (microcrystalline particulates having a particle size of about 0.1 $\mu$m to about 1.2 $\mu$m in rutile-type, anatase-type or brookire type, etc.), barium sulfate particulates, aluminum particulates and microflakes, and particulates having light-shielding ability include carbon black, gas black and carbon particulates. Among them, titanium dioxide particulates and barium sulfate particulates are preferred.

As the hydrophilic polymer binder having film-forming ability, there are the aforementioned hydrophilic polymers, and regenerated cellulose, cellulose acetate and the like which are weakly hydrophilic. Preferred ones are gelatin, gelatin derivatives, polyvinyl alcohol, polyacrylamide, maleic acid copolymers and the like. In the case of gelatin and gelatin derivatives, a known hardening agent (crosslinking agent) may be added.

6. Analytical element having a layer construction of the above 1–4 provided with water-impermeable gas-permeable layer (barrier layer) between hydrophilic polymer layer and spreading layer:

This analytical element is effective for the analysis of BUN (urea nitrogen) and CRE (creatinine) evolving ammonia gas, $CO_2$, etc. Either of whole blood and plasma can be used as samples. The barrier layer applicable to the invention includes the uniform coating layer of an uniform polymer disclosed in U.S. Pat. No. 4,066,403, membrane filter disclosed in U.S. Pat. No. 4,548,906 and the like.

In this invention, the measuring reagent means the reagent which directly reacts with analyte to produce a chemical change. That is, in the case that an enzyme is analyte, the measuring reagent is a substrate thereof, and in the case that analyte is an antigen (antibody), it is an antibody (antigen). In the case that detecting reaction is initiated by an enzyme, the measuring reagent is the enzyme, and in the case that detecting reaction is induced by a general chemical reaction, it is the corresponding chemical substance. Examples are shown below:

In the case that analyte is GOT, the measuring reagent is aspartic acid and glutamic acid, and in the case of amylase, it is starch having a high molecular weight or origosaccharide having a low molecular weight. In the case of GGT, it is paranitrophenyl anilide, and in the case of ALP, it is paranitrophosphophenyl anilide, etc. In the case of glucose, it is glucose oxidase, and in the case of uric acid, it is urtcase. In the case of cholesterol, it is cholesterol esterase or cholesterol oxidase, in the case of neutral fats, it is lipase or esterase, etc. In the case that an indicator directly reacts with analyte, such as protein, albumin, Ca, inorganic phosphorus, etc. it is the indicator. Although the above reagents may be incorporated into the analytical reagent, in many cases, the stability of the product after reaction is degraded. Therefore, it is advantageous that the measuring reagent solution is separately prepared.

Since an object of the invention is to prevent degradation of the detecting reagent during stock which is a defect of conventional analytical elements, if a reaction reagent incorporated into the analytical element is unstable, such as some enzymes, the reaction reagent is preferably incorporated into the measuring reagents solution. That is, with respect to the distribution between the reagents to be incorporated into the measuring reagents solution and those to be incorporated into the analytical element, it may be varied using analytical performance and stock stability as an indicator. In the case of one analyte, the above distribution differs according to the construction of detecting reaction system.

Various reagents may be incorporated into the measuring reagents solution in order to adjust pH or ion strength so that reaction proceeds stably to obtain a good reproducibility, in order to improve diffusion and permeation into the materials constructing the analytical element, in order to improve the unstability of enzyme, etc. contained therein, or the like. Reagents for inhibiting reactions competitive to the detecting reaction may also be incorporated. As such a reagent, there are bilirubin oxidase, ascorbate oxidase, etc. Furthermore, a compound inhibiting an enzyme derived from a certain organism, such as an inhibitor of p-type amylase, may be added in order to detect an isozyme. In the case of measuring whole blood samples, $NaN_3$ or the like may be added which is effective as the inhibitor of catalase activity of hemoglobin.

In view of manufacturing, packaging, transportation, store, measuring operations, etc., the multilayer analytical element of the invention is preferably cut into square or circular pieces having a side or diameter of about 15 mm to about 30 mm, and put in a slide frame as disclosed in Japanese Patent KOKAI No. 57-63452, U.S. Pat. Nos. 4,169,751, 4,387,990, PCT application WO 83/00391, etc. for use. However, it may be formed into a stick similar to urine test paper, etc.

In the case that the period from the supply of a liquid sample to the supply of measuring reagents is long, it is preferred that the analytical element is dried for a fixed time under substantially fixed conditions after the supply of a liquid sample. Preferable drying methods and conditions are disclosed in detail in Japanese Patent KOKAI No. 3-289543 from page 25, line 9 to page 28, line 6, particularly from page 27, line 13 to page 28, line 6. A particularly preferred method is heating the analytical element is placed in an enclosure so that the circumference of the analytical element is covered. By employing this method, substantially constant dried state can be obtained without the influence of environmental temperature and moisture. A suitable temperature range is 10° to 60° C., preferably 20° to 45°, more preferably 30° to 40° C. A suitable temperature variation through the incubation is $\pm 5°$ C., preferably $\pm 3°$ C., more preferably $\pm 1°$ C.

An incubator suitable for the above incubation which is carried out under substantially fixed conditions is disclosed in Japanese Utility Model KOKAI No. 3-126499. The incubator is composed that an analytical element is placed in its receiving portion, heated by a heating means, and kept at a constant temperature. The incubator is provided with a detachable cover which can seal the element-receiving portion at the upper part of the receiving portion, and the volume of the space formed in the element-receiving portion closed by the cover is designed so as to almost conform to the volume of the analytical element. Similar good reproducible results can be obtained by blowing dried air with a fixed temperature under substantially fixed conditions, but this method is disadvantageous because of expensiveness compared with the above incubator.

Hereupon, "dried" is in the state that reactions substantially do not proceed or that degradation of analyte does not proceed. Therefore, it is different according to analyte, and for example, in the case of enzymes, moisture content in the hydrophilic polymer is less than 50%, preferably less than 20%, more preferably less than 10%.

In the case that the period from the analytical element which was made in the state that reactions substantially do not proceed to the supply of the measuring reagents solution is long, for example, in the case that the analytical element is mailed to a hospital or the like, the analytical element is necessary to be kept in the conditions substantially excluding moisture and air. The details of the preservation are also disclosed in Japanese Patent KOKAI No. 3-289543 from page 28, line 12 to page 30, line 11. For example, a means is of sealing the analytical element in a box made of metal or a bag made of a water-impermeable organic polymer or metal film or sheet provided with a moisture-removing means. As the moisture-removing means, a moisture absorbing agent which Substantially does not denature the analyte is selected from known ones, and placed it. Another means to get out the air in the bag by wiping sufficiently after the analytical element is put therein.

The analysis using the aforementioned dry analytical element is conducted by the following method. To the analytical element supplied with a liquid sample which is not dried or is dried or is taken out from the above sealed container, the measuring reagents solution corresponding to the analytical item is supplied. Reaction occurs, and the analyte contained in the sample is determined by measuring the reaction using a known method (reflection photomerry, color change, fluorometry, emission photomerry, etc.) in the dry analysis method.

As the measuring reagents solution, a known reagents solution in the wet analysis can be used. The reagents react with the analyte to produce a change, mainly a change detectable by an optical measuring method, such as color change, coloring, fluorescence, luminescence, absorption wave length change in ultraviolet region, generation of turbidity, etc.

As the measuring method in the dry analysis, reflection optical system is usually employed. In the method of the invention, the photomerry conducted through the water-impermeable support of the analytical element has the widest application range. However, in the case that the sample is not whole blood or that measurement is conducted after removing the spreading layer, the measurement can be conducted by measuring transmitted light. When the water-impermeable support is opaque, the measurement can be conducted from the side opposite to the support.

The preservation of the dry analytical element in the invention can be utilized in every field corresponding to the aforementioned Groups 1 through 3, and it is also effective in the clinical medical assay in the inspection at home.

In the case that blood is used as the sample, since dry analytical elements need a very small amount of blood, blood can be drawn by using a suitable device such as a capillary pipette. When the dry analytical element is applicable to whole blood, the blood drawn can be used as the liquid sample for measuring as it is, and therefore, the element is particularly effective for the inspection at home system. When the dry analytial element is for plasma or serum, plasma or serum is separated from the blood drawn by centrifuging or standing, and used as the liquid sample for measuring. Body fluids other than blood, such as urine and saliva, a suitable amount is placed in a container, and directly used as the sample.

Figure 1:
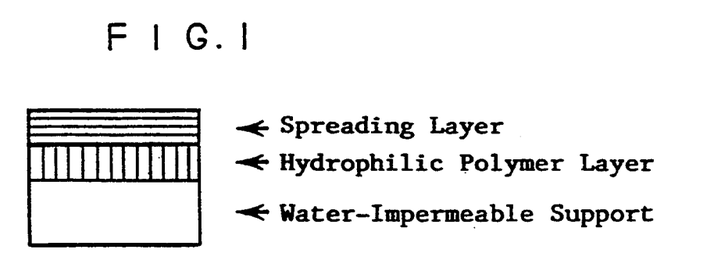
FIGS. 1 through 4 are partially sectional views of analytical elements which are applicable to the invention.
Figure 2:
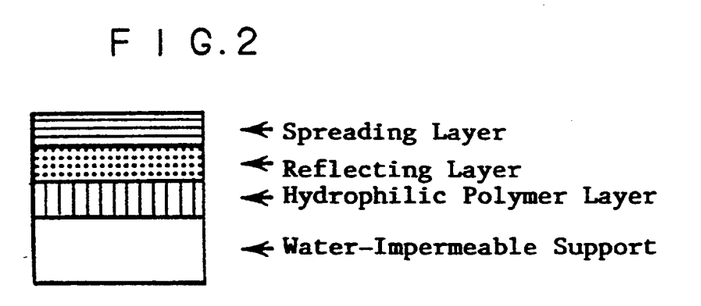
Figure 3:
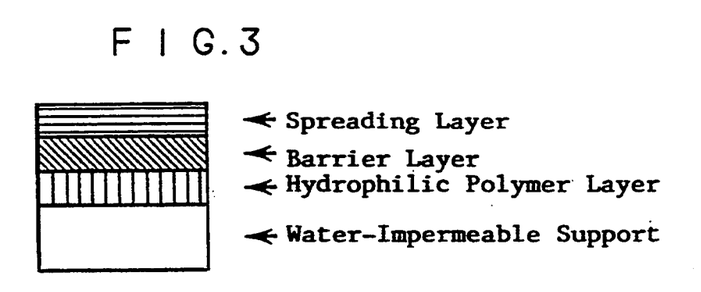
Figure 4:
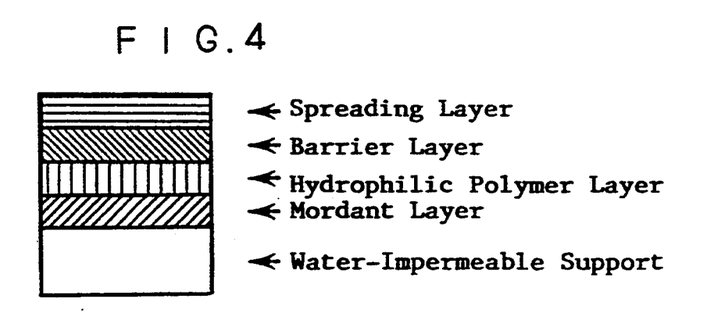
Figure 5:
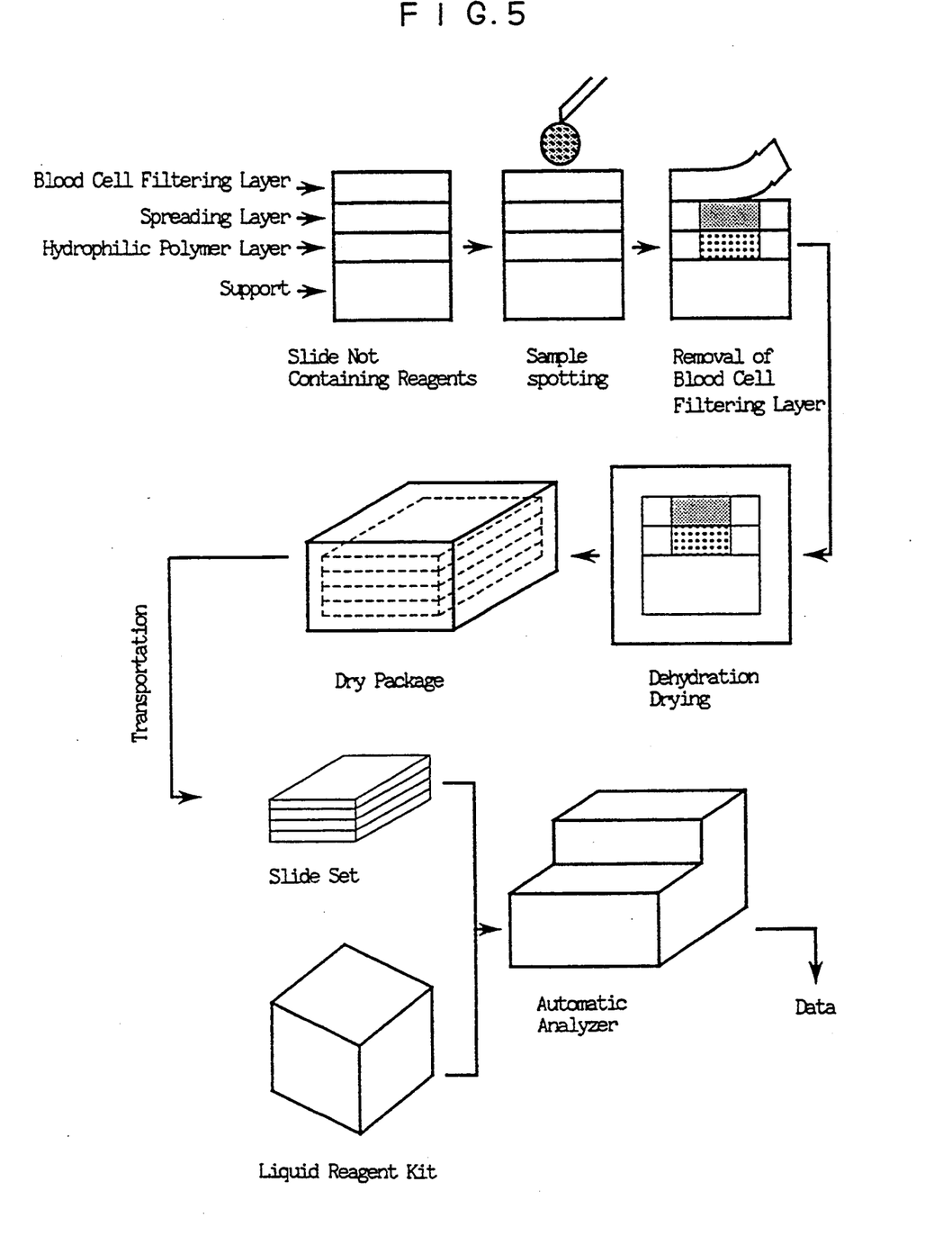
FIG. 5 is a schematic illustration indicating a procedure of the invention.

The above samples are supplied to the dry analytical element used in the invention, preserved according to the method of the invention, transported if necessary, and analysis by the method mentioned previsouly. It is possible to transport by mail or courier, and sufficiently applicable to the inspection at home system. A procedure of the method of the invention is shown in FIG. 5. The analytical element is composed of a blood cell filtering layer, a spreading layer, a hydrophilic polymer layer and a support laminated in this order, and measuring reagents are not incorporated. A whole blood sample is spotted onto the blood cell filtering layer of the analytical element, and the blood cell filtering layer is peeled off. Then, the analytical element is dried to dehydrate, and packed in a package capable of keeping the dried state. The package is transported, and the analytical element is set in an automatic analyzer together with the measuring reagents solution. Then, analysis is conducted, and the result is obtained.

Since the dry analytical element used in the invention does not contain unstable measuring reagents, the shelf life is greatly improved compared with conventional dry analytical elements. Besides, since the measuring reagents used in the conventional wet analysis can be used, it is not necessary to develop analytical elements for each measuring item. Moreover, one kind of analytical element can be applied to many items, and therefore, it is inexpensive.

EXAMPLES

Example 1 Measurement of Urea Nitrogen (BUN) in Plasma

Preparation of Measuring Reagents Solution

Urease manufactured by Toyo Boseki was dissolved in 10 mM phosphate buffer containing 0.5% Triton X-100 to prepare an UN reagent solution having 75,000 U/l urease activity. After the preparation, each 500 μl of the solution was piperted into plastic tubes, and stocked in a freezed state at $-80°$ C.

Preparation of Standard Solution for Plasma

Private control sera CP-L, CP-M and CP-H (manufactured by Fuji Photo Film Co., Ltd.) for "Fuji Dry Chem" were used as the samples. Their BUN value was measured using "Hitachi 7050" (manufactured by Hitachi Ltd.), and found that 11.4 mg/dl, CP-M=67 mg/dl and CP-H=101 mg/dl.

Preparation of Analytical Element

Onto a transparent PET film 180 μm in thickness, the following undercoating layer was applied, and then dried.

| Undercoating Layer | |
|---|---|
| Polyvinylmethyl ether | 0.035 g/m$^2$ |
| (Weight average molecular weight: About 40,000) | |
| p-Chlorophenol | 0.7 g/m$^2$ |

The following indicator layer was applied thereonto as an aqueous solution, and then dried.

| Bromophenol Blue | 0.340 g/m$^2$ |
|---|---|
| Vinyl acetate-ethyl acrylate copolymer latex | 8.5 g/m$^2$ |

Subsequently, polyethylene membrane filter having a mean pore size of 0.2 μm, a void content of 75% and a thickness of 100 μm was superposed on the indicator layer, and uniformly pressed to form a barrier layer.

Onto the barrier layer, the following reagent layer was applied as an aqueous solution, and then dried.
Reagent Layer

| Reagent Layer | |
|---|---|
| Hydroxyethyl cellulose | 16 g/m$^2$ |
| (Weight average molecular weight: About 40,000, mean substitution degree (DS) of hydroxyethyl groupL 1.0–1.3, mean mol substitution (MS): 1.8–2.5) | |
| Sodium tetraborate | 4 g/m$^2$ |
| pH 10.0 | |

The above reagent layer was almost uniformly swelled by 0.2% p-nonylphenoxypolyglycidol aqueous solution, and immediately, knitted fabric (gauge number: 40, 25% weight loss by treating with aqueous NaOH solution) was superposed, and uniformly laminated by passing between press rollers.

Furthermore, the following polyvinylpyrrolidone ethanol solution was applied to impregnated into the laminate for the purpose of improving spreading ability, and dried to prepare an integral multilayer analytical element for the determination of ammonia.

| Polyvinylpyrrolidone | 7.76 g/m$^2$ |
|---|---|

(Mean molecular weight: about 1,200,000)

Spotting of Sample and Drying

10 μl of the standard solution prepared above was sucked into a micropipette, and spotted onto the analytical element prepared in . The analytical element was set in an incubator for drying and fixation (Fuji Photo Film Co., Ltd.), and left for 10 minutes to dry the sample in the analytical element.

Measurement

Figure 6:
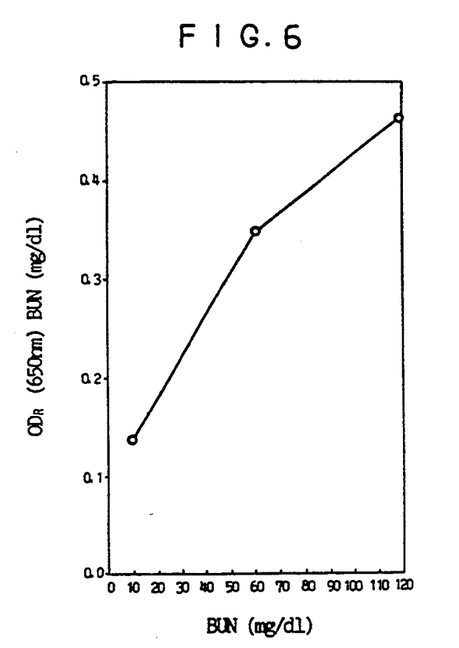
FIG. 6 is a graph indicating a relation between the urea nitrogen concentration of a sample measured by the solution method and reflective optical density.

The analytical element dried in the above was set in "Fuji Dry Chem 5500" analyzer. The urease solution prepared in was sucked into a piperting apparatus, and spotted. The analytical element was incubated, and then, reflection optical density was measured at the wave length of 650 nm according to usual operations. The difference between the density after 1 minute from the initiation of reaction and that after 6 minutes was calculated to obtain the relation between the urea nitrogen concentration of the sample and the reflection optical density (calibration curve) shown in FIG. 6.

Preparation of Whole Blood-Plasma Samples Varying Urea Concentration

Heparin was used as the anticoagulant, and 10 ml of vein blood was drawn from 2 healty persons. Separately, 10 urea aqueous solution was prepared by dissolving in a saline solution. The vein blood was divided into 5 containers in amount of each 2 ml, and aqueous urea solutions were put therein to prepare samples in 5 concentration levels.

Furthermore, 1 ml of whole blood samples in each level was taken, and centrifuged to prepare plasma samples. The urea concentration of the plasma samples were measured by "Hitachi 7050" (Hitachi Ltd.), and that of the whole blood samples were measured by "Fuji Dry Chem 5000" (Fuji Photo Film Co., Ltd.).

Preparation of Relationship Figure

10 μl of the plasma and whole blood samples obtained in was spotted onto the analytical element, and dried and fixed according to the same procedure as . Subsequently, the urease solution was spotted, incubated, and the reflection optical density was measured after 1 minute and after 6 minutes similar to .

Calculation of Urea Nitrogen Concentration

Using the calibration curve obtained in , the urea nitrogen concentration in the plasmas were determined. As to the whole blood samples, a calibration curve was prepared by a comparison of the measured value of "Fuji Dry Chem 5000" as to the sample 1 with the optical density obtained in , and the urea nitrogen concentration was determined as to the sample 2.

Preparation of Relationship Figure

Figure 7:
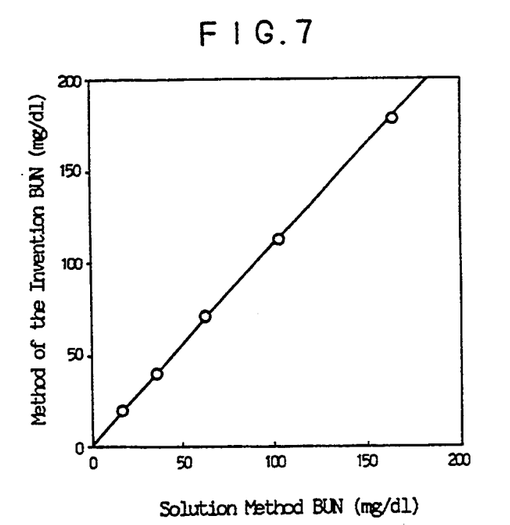
FIG. 7 is a graph indicating a relation between the urea nitrogen concentration of a plasma sample measured by the method of the invention and that measured by the solution method.
Figure 8:
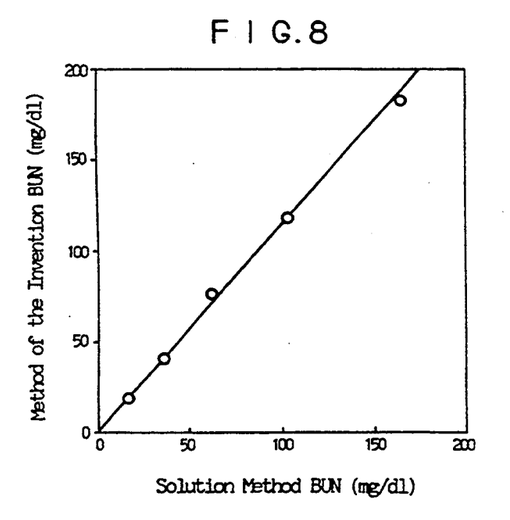
FIG. 8 is a graph indicating a relation between the urea nitrogen concentration of a whole blood sample measured by the method of the invention and that measured by the solution method.

The relationship between the measured values of "Hitachi 7050" and the measured values of the Invention as to the plasma samples and the whole blood samples are as shown in FIGS. 7 and 8, and a good relationship was obtained in both cases.

10 Evaluation of Stability with Time

Figure 9:
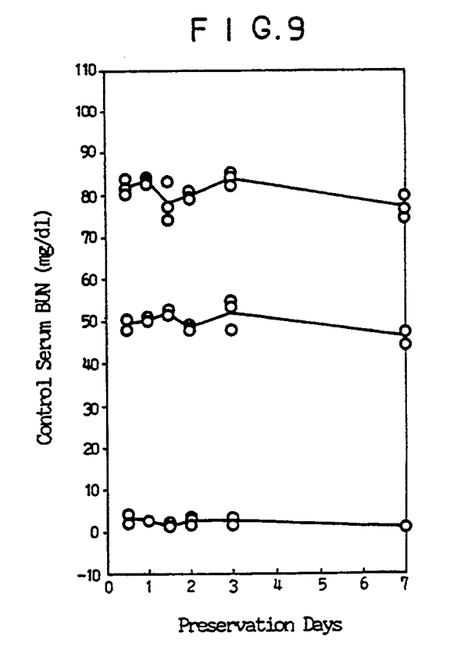
FIG. 9 is a graph indicating a relation between the preservation period and the measured value of urea nitrogen concentration of a control serum.

According to the same operation as , private control sera CP-L, CP-M and CP-H for "Fuji Dry Chem" were spotted onto each 30 pieces of the analytical element and dried. The analytical elements were divided into each three piece group, and each group was put in a polyethylene pouch together with 2 g of silica gel. The pouches were left in a drawer of a laboratory table at room temperature. The pouches were gradually taken out with passing days, and the urea nitrogen concentration was measured by the procedure of . The relationship between the passed days and the measured values is an shown in FIG. 9. It can be seen that a measured value having good reproducibility can be obtained at least for several days by preserving in a dried state after spotting according to the method of the invention, even leaving the analytical element at room temperature.

Figure 10:
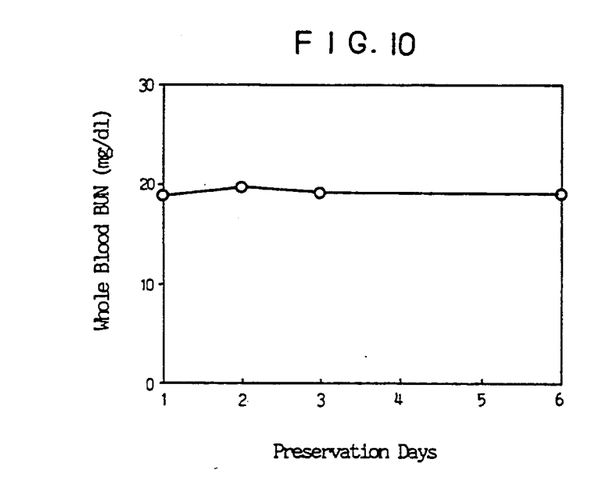
FIG. 10 is a graph indicating a relation between the preservation period and the measured value of urea nitrogen concentration of a whole blood sample.

As to the whole blood samples, they were treated similar to the control sera, and the stability with time was evaluated. As shown in FIG. 10, the results having good reproducibility were obtained.

11 Evaluation of Simultaneous Reproducibility

The standard solutions prepared similar to the above were spotted onto the dry analytical elements, and dried. They were measured according to the procedure of , and the dispersion of the measured values was examined. The results are shown in Table 1, and they were good results.

TABLE 1

|  | CP-L | CP-M | CP-H | mg/dl |
| --- | --- | --- | --- | --- |
| 1 | 9.8 | 67.0 | 114.4 | |
| 2 | 8.3 | 67.8 | 119.3 | |
| 3 | 10.8 | 67.4 | 118.6 | |
| 4 | 9.8 | 64.2 | 117.3 | |
| 5 | 10.4 | 59.8 | 117.9 | |
| 6 | 8.1 | 60.0 | 122.8 | |
| 7 | 8.3 | 62.2 | 116.2 | |
| 8 | 11.3 | 55.2 | 121.2 | |
| 9 | 9.2 | 60.0 | 122.2 | |
| 10 | 10.8 | 58.3 | 124.3 | |
| $\overline{X}$ | 9.68 | 62.19 | 119.41 | |
| SD | 1.11 | 4.06 | 2.98 | |
| CV | 11.4 | 6.5 | 2.5 | |

Example 2 Measurement of Creatinine (CRE)

Preparation of Measuring Reagents Solution

Creatinine imino hydrolase manufactured by Toyo Boseki was dissolved in 10 mM phosphate buffer containing 0.5% Triton X-100 to prepare a CRE reagent solution having 65,000 U/l enzyme activity.

Preparation of Calibration Curve

Figure 11:
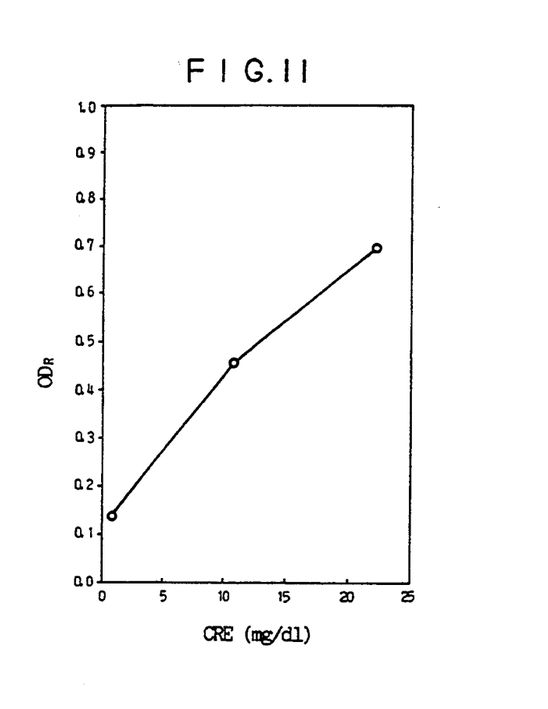
FIG. 11 is a graph indicating a relation between the creatinine concentration of a control serum measured by the solution method and reflective optical density.

The relationship between the reflection optical densities and the measured values of "Hatachi 7050" was determined according to the procedures of , and of Example 1. The results are as shown in FIG. 11, and a good relationship was obtained.

Measurement of Whole Blood-Plasma Samples

Figure 12:
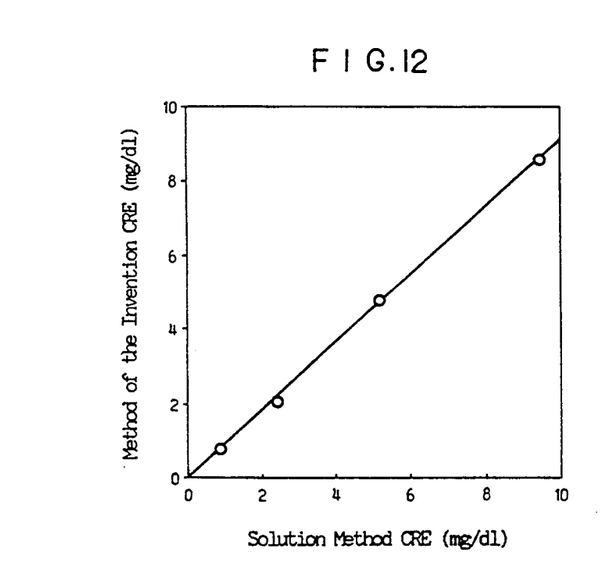
FIG. 12 is a graph indicating a relation between the creatinine concentration of a plasma sample measured by the method of the invention and that measured by the solution method.

Using heparin as the anticoagulant, vein blood was drawn with healthy persons, and centrifuged to obtain plasma. The plasma was used as the sample, and reflection optical density was determined similar to of Example 1. The CRE concentration in the samples were calculated using the calibration curve prepared in the above . Simultaneously, the CRE concentration were measured by using "Hitachi 7050". The results are shown in FIG. 12.

Example 3 Measurement of GGT

Preparation of Analytical Element Onto a transparent film base of polyethylene terephthalate 180 μm in thickness provided with undercoating, gelatin containing 0.2% of nonionic surfactant p-nonylphenoxypolyglycidol (containing 10 glycidol unit on average) was applied so that the dry thickness was about 15 μm, and dried. Polyester knitted fabric which was made hydrophilic by using surfactant was laminated thereonto according to the method disclosed in Japanese Patent KOKAI No. 62-224299. 7% polyvinylpyrrolidone (mean molecular weight: 1,200,000) ethanol solution was applied onto the spreading layer so that the coating amount was 2 g/m².

The film was cut into square tips having a side of 15 mm, and placed in a plastic mount according to the method disclosed in Japanese Patent KOKAI No. 57-63452 to complete an analytical element.

Preparation of Measuring Reagents Solution

The following GGT measuring reagents solution was prepared.

| Tris(hydroxymethyl)aminomethane | 720 mg |
| --- | --- |
| Glycylglycine | 156 mg |
| L-α-glutamyl-3-carboxy-p-nitroaniline | 58.5 mg |
| Distilled water | 10 ml |
| pH 8.1–8.2 | |

Preparation of GGT Calibration Curve

Figure 13:
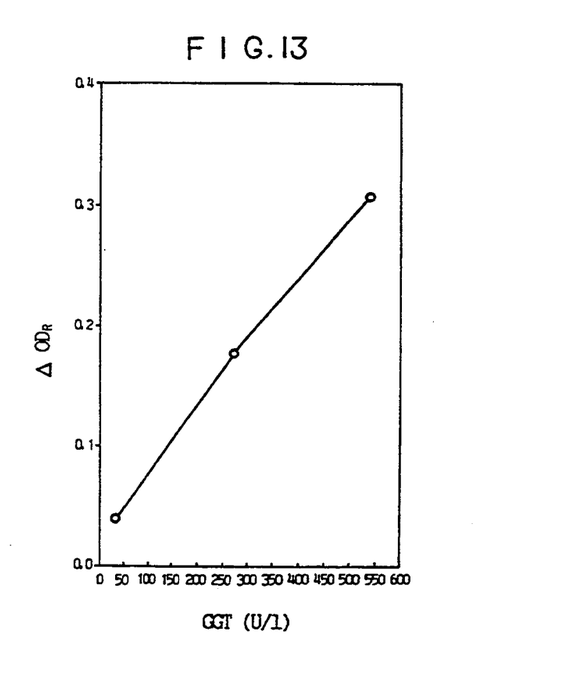
FIG. 13 is a graph indicating a relation between the GGT activity of a control serum measured by the solution method and reflective optical density.

A calibration curve was prepared similar to Example 1. The results are as shown in FIG. 13.

Evaluation of Simultaneous Reproducibility

Using the slides prepared in the above , simultaneous reproducibility was evaluated similar to Example 1. The results are as shown in Table 2.

TABLE 2

|  | CP-L | CP-M | CP-H | U/l |
| --- | --- | --- | --- | --- |
| 1 | 36 | 282 | 554 | |
| 2 | 35 | 343 | 697 | |
| 3 | 38 | 288 | 637 | |
| 4 | 39 | 328 | 618 | |
| 5 | 40 | 294 | 673 | |
| 6 | 34 | 308 | 641 | |
| 7 | 39 | 293 | 637 | |
| 8 | 34 | 297 | 602 | |
| 9 | 38 | 340 | 657 | |
| 10 |  | 314 |  | |
| $\overline{X}$ | 37.00 | 308.70 | 635.11 | |
| SD | 2.16 | 20.73 | 39.09 | |
| CV | 5.8 | 6.7 | 6.2 | |

Evaluation of Stability with Time

Figure 14:
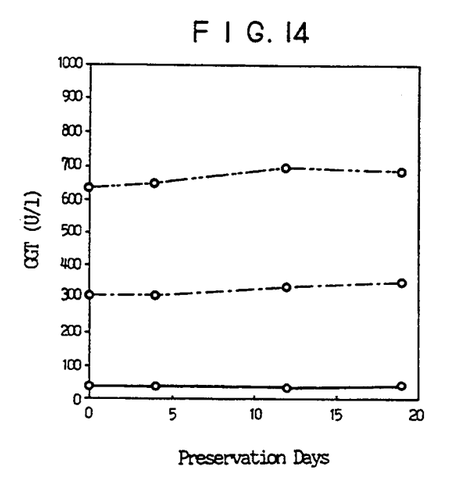
FIG. 14 is a graph indicating a relation between the preservation period and the measured value of GGT activity of a plasma sample.

Using the analytical element prepared in the above , stability with time was evaluated similar to Example 1. The results are as shown in FIG. 14, and a good stability with time was shown.

Example 4 Measurement of GOT

Preparation of Analytical Element

A film was prepared similar to 1 of Example 3, and 5% a leuco imidazole dye, 1-(3,5-dichlorophenyl)-2,3-dimethyl-4-amino-3-pyrazoline-5-one was further applied thereonto as the indicator for detection, followed by drying. The concentration of the indicator for detection was about 1 g/m².

Preparation of Measuring Reagents Solution

The following GOT measuring reagents solution was prepared.

| Tris(hydroxymethyl)aminomethane | 84 mg |
| --- | --- |
| Monopotassium dihydrogen phosphate | 104 mg |
| L-Aspartic acid | 431 mg |

| | |
|---|---|
| α-Ketoglutaric acid · 2Na | 93 mg |
| 20% magnesium chloride | 273 μl |
| Peroxidase | 3431 U |
| Thiamine pyrophosphate | 21 mg |
| Flavin adenine dinucleotide | 5 mg |
| Oxaloacetate oxidase | 24 U |
| Pyruvate oxidase | 3088 U |
| 1N Sodium hydroxide | 3.4 ml |
| Triton X-100 | 100 mg |
| Distilled water | 6.6 ml |
| pH 7.5 | |

Preparation of GOT Calibration Curve

Figure 15:
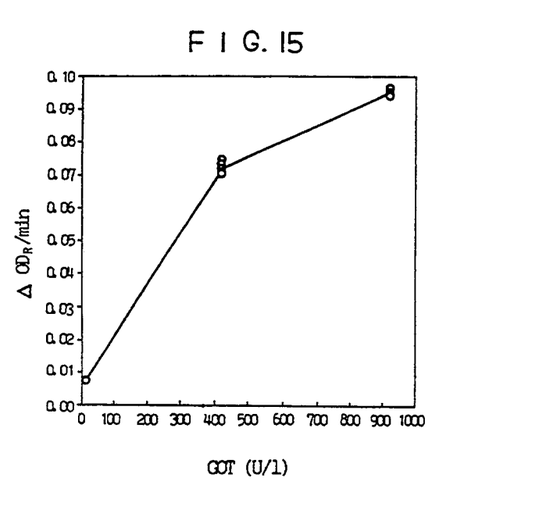
FIG. 15 is a graph indicating a relation between the GOT activity of a sample measured by the solution method and reflective optical density.

A calibration curve was prepared similar to of Example 2. The results are as shown in FIG. 15.

Example 5 Measurement of GPT

Preparation of Analytical Element

Onto a transparent film base of polyethylene terephthalate 180 μm in thickness provided with undercoating, gelatin containing 0.2% of nonionic surfactant p-nonylphenoxypolyglycidol (containing 10 glycidol unit on average) and 0.1% leuco imidazole dye was applied so that the dry thickness was about 15 μm, and dried. A light-reflecting layer composed of $TiO_2$ particulates, surfactant and gelatin was applied thereonto so that the dry thickness was about 5 μm, and gelatin was applied thereonto, followed by drying. Polyester knitted fabric which was made hydrophilic was wet laminated similar to aforementioned to prepare an analytical element film. The film was processed by the method similar to aforementioned to prepare analytical elements.

Preparation of Measuring Reagents Solution

The following GPT measuring reagents solution was prepared.

| | |
|---|---|
| Tris(hydroxymethyl)aminomethane | 87 mg |
| Monopotassium dihydrogen phosphate | 103 mg |
| L-Alanine | 620 mg |
| α-Ketoglutaric acid · 2Na | 93 mg |
| 20% magnesium chloride | 275 μl |
| Peroxidase | 3416 U |
| Thiamine pyrophosphate | 21 mg |
| Flavin adenine dinucleotide | 5 mg |
| Pyruvate oxidase | 3088 U |
| Triton X-100 | 100 mg |
| Distilled water | 10 ml |
| pH 7.5 | |

Preparation of GPT Calibration Curve

Figure 16:
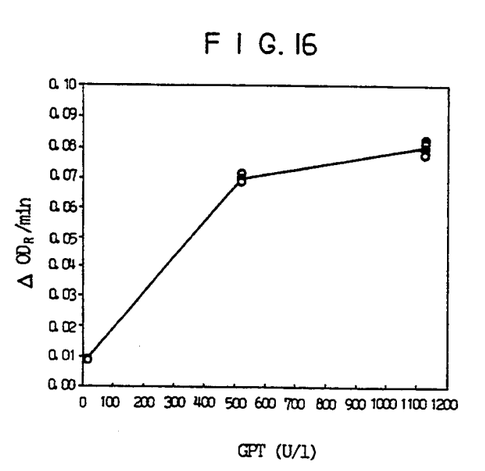
FIG. 16 is a graph indicating a relation between the GPT activity of a sample measured by the solution method and reflective optical density.

A time course of GPT was measured similar to of Example 2, and a calibration curve was prepared by the difference of optical density from 2.5 minutes to 4 minutes, as shown in FIG. 16.

Evaluation of Preservation Stability

Figure 17:
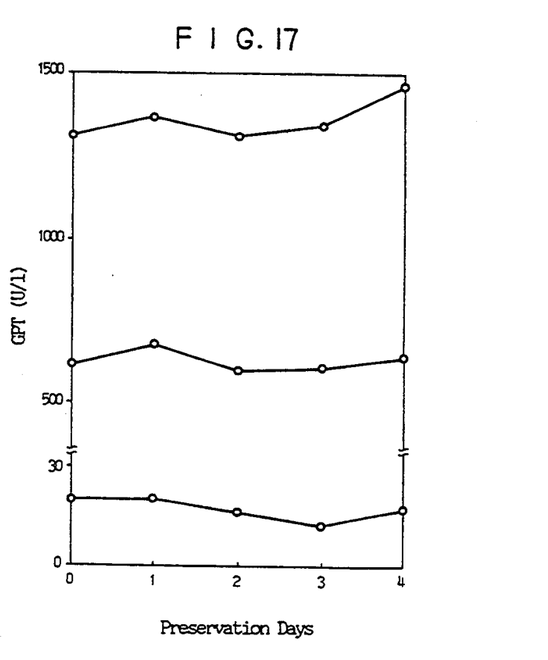
FIG. 17 is a graph indicating a relation between the preservation period and the measured value of GPT activity of a control serum.

Preservation stability was evaluated in the case of leaving the analytical element at room temperature after spotting and drying similar to 10 of Example 1. The results are shown in FIG. 17.

Example 6 Measurement of Ca

Preparation of Calibration Curve

Figure 18:
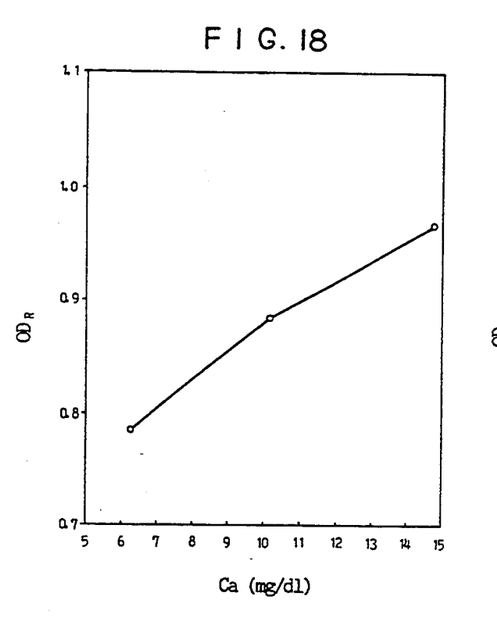
FIG. 18 is a graph indicating a relation between the calcium concentration of a sample measured by the solution method and reflective optical density.

Using the analytical element prepared similar to of Example 3 and the following Ca measuring reagents solution, a calibration curve was prepared according to the procedure similar to of Example 1 wherein private control sera CP-L, CP-M and CP-H for Fuji Dry Chem were used as the samples. The results are as shown in FIG. 18.

| | |
|---|---|
| o-Cresol phthalein complexon | 90 mg |
| 0.4 M CAPS (pH 10.5) | 10 ml |

Simultaneous reproducibility was evaluated similar to of Example 1. The results are shown in Table 3.

TABLE 3

| | CP-L | CP-M | CP-H |
|---|---|---|---|
| 1 | 5.6 | 10.1 | 15.1 |
| 2 | 8.1 | 10.4 | 17.2 |
| 3 | 5.0 | 8.5 | 13.4 |
| 4 | 5.7 | 10.7 | 15.5 |
| 5 | 5.6 | 8.6 | 16.6 |
| 6 | 6.0 | 10.1 | 12.6 |
| 7 | 7.5 | 9.3 | 15.3 |
| 8 | 5.5 | 11.3 | 13.5 |
| 9 | 7.1 | 12.7 | 15.6 |
| 10 | 6.9 | 11.9 | 13.4 |
| X̄ | 6.30 | 10.36 | 14.82 |
| SD | 0.97 | 1.29 | 1.45 |
| CV | 15.4 | 12.5 | 9.8 |

Example 7 Measurement of Total Cholestrol (TCHO)

Preparation of Analytical Element

Analytical element was prepared similar to of Example 5, but peroxidase was added together with imidazole leuco dye so that the coating amount was 50,000 $U/cm^2$.

Preparation of Measuring Reagents Solution

The following TCHO measuring reagents solution was prepared.

| | |
|---|---|
| Cholesterol esterase | 987 U |
| Cholesterol oxidase | 600 U |
| Triton X-100 | 500 mg |
| Phosphate buffer (50 mM, pH 7.5) | 10 ml |

Preparation of Calibration Curve

Figure 19:
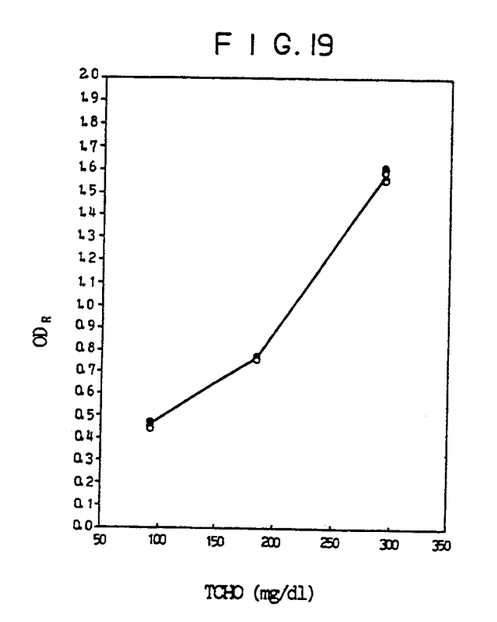
FIG. 19 is a graph indicating a relation between the total cholesterol concentration of a sample measured by the solution method and reflective optical density.

Similar to of Example 1, a calibration curve was prepared. The results are as shown in FIG. 19.

Evaluation of Simultaneous Reproducibility

Similar to 11 of Example 1, simultaneous reproducibility was evaluated. The results are as shown in Table 4.

TABLE 4

| | | | mg/dl |
|---|---|---|---|
| | CP-L | CP-M | CP-H |
| 1 | 91 | 185 | 294 |
| 2 | 90 | 182 | 295 |
| 3 | 96 | 186 | 298 |
| 4 | 94 | 185 | 283 |
| 5 | 94 | 186 | 291 |
| 6 | 87 | 178 | 295 |
| 7 | 93 | 182 | 291 |
| 8 | 96 | 185 | 292 |
| 9 | 95 | 185 | 297 |
| 10 | 93 | 186 | 290 |
| X̄ | 92.95 | 184.03 | 292.59 |
| SD | 2.83 | 2.44 | 4.38 |
| CV | 3.0 | 1.3 | 1.5 |

Evaluation of Simultaneous Reproducibility Using Whole Blood

Using vein blood drawn from healthy persons with heparin as the samples, simultaneous reproducibility was evaluated. 0.1% $NaN_3$ was added to the measuring reagents solution The results are as shown in Table 5.

TABLE 5

|   | mg/dl |
|---|---|
| 1 | 123.5 |
| 2 | 116.6 |
| 3 | 110.8 |
| 4 | 112.0 |
| 5 | 113.2 |
| 6 | 104.8 |
| 7 | 111.1 |
| 8 | 108.8 |
| 9 | 118.7 |
| 10 | 110.8 |
| x | 113.03 |
| SD | 5.05 |
| CV | 4.5 |

Example 8 Measurement of GPT in Whole Blood

Preparation of Analytical Element

Analytical element was prepared similar to of Example 5, but 1% NaN₃ aqueous solution was applied onto the spreading layer of polyester knitted fabric which was made hydrophilic so that the coating amount was 100 g/m², and after drying, it was processed into a slide.

Preparation of Measuring Reagents Solution

Similar to of Example 5, the GPT measuring reagents solution was prepared.

Preparation of Whole Blood Samples

Vein blood drawn from healty persons with heparin was divided into 3 sample tubes each in an amount of 1.5 ml. Private control sera CP-L, GP-M and CP-H for Fuji Dry Chem were dissolved using 1.5 ml of distilled water which is a half of normal dilution liquid amount of 3 ml, and mixed with the above whole blood to prepare whole blood samples different in GPT concentration. A part of each concentration level was centrifuged, and the GPT activity of the plasma was measured using "Hitachi 7050".

Supply of Sample and Drying

10 μl of the whole blood samples prepared in the above was spotted, and dried, similar to of Example 1.

Measurement

The analytical element obtained in the above was set in "Fuji Dry Chem 5500" analyzer, similar to of Example 1, and the measuring reagents solution prepared in the above was spotted. Reflection optical density was measured at 650 nm with time as the function of the incubation time, and a time course was obtained.

Preparation of Calibration Curve

Figure 20:
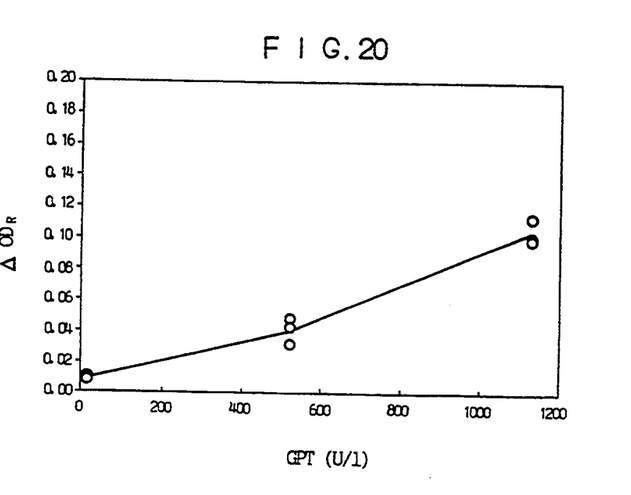
FIG. 20 is a graph indicating a relation between the GPT activity of a sample measured by the solution method and reflective optical density.

The relationship between the GPT activity value of the plasmas measured by "Hitachi 7050" and the reflection optical density difference ($\Delta OD_R$) between that after 5 minutes and that after 1 minute from the start of measurement is shown in FIG. 20.

Measurement of Whole Blood Sample

The untreated whole blood of the healthy persons used in the above was measured by the operation similar to the above , , and the activity value was calculated using the calibration curve obtained in and found to be 26 U/l.

On the other hand, the plasma was separated from the same whole blood by centrifuging, and the GFT activity was measured by using "Hitachi 7050" and found to be 25 U/l to confirm that the measured value according to the method of the invention is fully reliable.

EXAMPLE 9

In an experiment similar to Example 4, the measuring reagents solution was immediately added to the analytical element after spotting the sample without drying, and measured.

The inclination of the calibration curve was about 2/3 of the results of Example 4, but results having a good relationship were obtained between $\Delta OD_R$ and the measured values by "Hitachi 7050".

EXAMPLE 10

In the measurement of Ca in Example 6, microporous membrane made of cellulose acetate ("Fuji Microfilter FM 300", Fuji Photo Film Co., Ltd.) was use as the spreading layer instead of the polyester knitted fabric which was made hydrophilic, and the other procedures were the same as Example 6.

The simultaneous reproducibility (n=10, CV) was CP-L 2.7%, CP-M: 2.2%, CP-H: 3.1%, and it was confirmed that quantitative measurement is possible in the case of using membrane filter as the spreading layer.

I claim:

1. A method for quantitatively measuring an analyte using a dry analytical element which comprises:

supplying a measuring reagent solution to an analytical element comprising at least a hydrophilic polymer layer and a spreading layer which functions to evenly spread components contained in an aqueous liquid sample to supply the components to the hydrophilic polymer layer at a constant rate per unit area, said measuring reagent reacting directly with analyte in the liquid sample to produce a chemical change which is optically detectable, the analytical element having been prepared by applying a liquid sample comprising blood to the element and then drying the element under a drying temperature of from 10° to 60° C. up to a moisture content of the hydrophilic polymer of less than 20% to fix the sample thereon prior to supplying the reagent solution thereto; and optically measuring the chemical change.

2. The method of claim 4 wherein the analytical element comprises at least a water-impermeable gas-permeable layer which is provided between the hydrophilic polymer layer and the spreading layer.

3. The method of claim 1 wherein the analytical element further comprised a light-shielding layer which is provided between the hydrophilic polymer layer and the spreading layer.

4. The method of claim 1 wherein the dry analytical element comprises a hydrophilic polymer layer and a spreading layer laminated onto a water-impermeable support.

5. The method of claim 4 wherein the analytical element further comprises a water-impermeable, gas-impermeable layer between the hydrophilic polymer layer and the spreading layer.

6. The method of claim 5 wherein the analytical element further comprises a light shield layer between the hydrophilic layer and the spreading layer.

7. The method of claim 1 wherein the blood sample is plasma or blood serum.

8. The method of claim 1 wherein the analyte is an enzyme.

9. The method of claim 1 wherein the element is dried at a temperature from 30° to 40° C.

10. The method of claim 9 wherein the analyte of GOT or GGT.

11. The method of claim 1 wherein the drying is carried out in an incubator composed of an element-receiving portion, a heating means, a cover which seals the element-receiving portion at the upper part of the receiving portion, and wherein the volume of the space formed in the element-receiving portion may be closed by a cover so as to conform to the volume of the analytical element.

12. The method of claim 1 wherein the moisture content of the hydrophilic polymer is less than 10% after the drying step.

13. The method of claim 1 wherein the element is maintained in a non-folded state from the step of applying the liquid sample to the step of supplying the measuring reagent solution.

* * * * *